US006884241B2

United States Patent
Bertranou et al.

(10) Patent No.: US 6,884,241 B2
(45) Date of Patent: Apr. 26, 2005

(54) SPINAL ASSEMBLY PLATE

(75) Inventors: Patrick P. Bertranou, Beverly Hills, CA (US); Jean Yves Leroy, Beaurains (FR)

(73) Assignee: Orthotec, LLC, Beverly Hills, CA (US)

(*) Notice: Subject to any disclaimer, the term of this patent is extended or adjusted under 35 U.S.C. 154(b) by 119 days.

(21) Appl. No.: 09/945,915

(22) Filed: Sep. 4, 2001

(65) Prior Publication Data

US 2003/0045875 A1 Mar. 6, 2003

(51) Int. Cl.[7] ............................................. A61B 17/70
(52) U.S. Cl. ....................................................... 606/61
(58) Field of Search ........................ 606/60, 61, 69–71

(56) References Cited

U.S. PATENT DOCUMENTS

| | | | | |
|---|---|---|---|---|
| 1,025,008 A | * | 4/1912 | Miner ............................ | 606/71 |
| 4,790,297 A | * | 12/1988 | Luque ........................... | 606/61 |
| 5,129,899 A | * | 7/1992 | Small et al. .................... | 606/61 |
| 5,486,176 A | * | 1/1996 | Hildebrand et al. ............ | 606/71 |
| 5,584,887 A | * | 12/1996 | Kambin .......................... | 606/61 |
| 5,676,666 A | * | 10/1997 | Oxland et al. ................. | 606/61 |
| 6,645,207 B1 | * | 11/2003 | Dixon et al. ................... | 606/61 |

OTHER PUBLICATIONS

Steffee, Arthur D., M.D., "*VSP® (Variable Screw Placement)*", http://www.depuyacromed.com/products/degenerative/vsp.html, p.1 of 1, *DePuy AcroMed*.

\* cited by examiner

*Primary Examiner*—Eduardo C. Robert
*Assistant Examiner*—Michael B. Priddy
(74) *Attorney, Agent, or Firm*—Blakely, Sokoloff, Taylor & Zafman

(57) ABSTRACT

A spinal assembly plate. The plate can have an uninterrupted passage to accommodate a portion of a vertebral screw there through at a non-predetermined location of the plate. An apparatus can be included with sidewalls to secure the plate there between. Another apparatus can be included with a face having a frictional character to longitudinally stabilize the apparatus to the plate. A spinal assembly can be included having a vertebral screw, a spinal plate, an apparatus to secure the vertebral screw, and a connector brace to stabilize the plate. In a method of the invention, a vertebral screw can be placed through an opening of a connector brace and into a vertebral body of a patient wherein the brace includes sidewalls to stabilize a spinal plate.

13 Claims, 3 Drawing Sheets

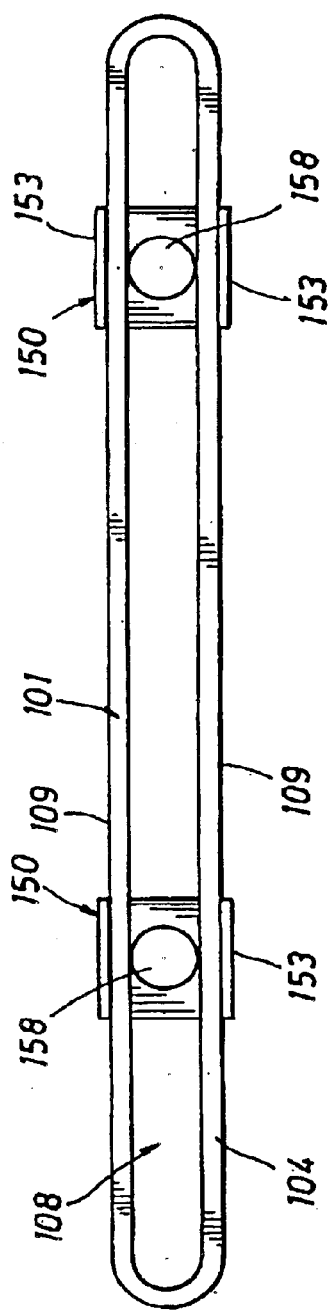

SPINAL ASSEMBLY PLATE

BACKGROUND

The invention relates to spinal implants. In particular, the invention relates to spinal fusion assemblies for the treatment of spinal injuries, deformities, or defects.

BACKGROUND OF THE RELATED ART

The spinal column, as with other orthopedic structures, is susceptible to a host of injuries, diseases, and malformations. For example, an individual may experience a herniated disk, spinal stenosis, scoliosis, fracture, or a dislocation of vertebrae of the spinal column. When such conditions are encountered, surgical treatment is often used to facilitate a degree of realignment of adjacent vertebrae. Following initial surgical treatment, spinal fusion devices or assemblies are often used to stabilize adjacent vertebrae of the spinal column and to facilitate further realignment.

Spinal fusion assemblies account for the morphology of the spinal column. For example, each vertebrae includes pedicle structures opposite one another. That is, a right pedicle structure of one vertebrae is adjacent a right pedicle structure of an adjacent vertebra, such that one row of pedicle structures of adjacent vertebrae is present at the right side of the spinal column. Similarly, a row of pedicle structures of adjacent vertebrae is present at the left side of the spinal column.

A spinal fusion assembly usually includes a pair of longitudinal plates, one to be secured to one row of pedicle structures and one to be secured to the other row of pedicle structures. Each plate of the assembly is positioned above, generally posterior, of adjacent pedicle structure rows. Each plate is secured to a corresponding row of pedicle structures by way of vertebral screws, often referred to as pedicle screws.

Implanting a spinal fusion assembly, such as that described above, immobilizes the adjacent vertebrae which have been secured to the plates by the vertebral screws. This encourages a natural fusion of these vertebrae to one another. Healing of the vertebrae takes place as the vertebra are immobilized and become fused.

The plates of a spinal fusion assembly can be of a flat elongated solid body type. The plates include pre-drilled holes or notches to accommodate or guide vertebral screws through each plate and into the pedicle structures. Thus, the positioning of the pedicle screws is predetermined based on the location of the pre-drilled holes or notches. However, the position of each of the pedicle structures of a row of pedicle structures is unique to each patient. For example, the distance between adjacent pedicle structures can vary from patient to patient, and even within the same patient. That is, even within the same row of pedicle structures of a patient, variance in distance between adjacent pedicle structures is possible. This is, in fact, likely, due to the complex morphology often associated with spinal conditions requiring fusion. As a result, the pre-drilled holes of the plates are often not ideally located above the pedicle structure into which a vertebral screw is to be inserted. This can lead to improper placement of vertebral screws or the inability to place a vertebral screw at every pedicle structure of every vertebrae to be fused. Therefore, what is needed is an improved spinal assembly plate.

SUMMARY

In one embodiment, a spinal assembly plate is provided having an uninterrupted passage. The passage accommodates a portion of a vertebral screw at a non-predetermined location along the plate.

In another embodiment, an apparatus is provided with a first sidewall and a second sidewall. The sidewalls are to secure a plate of a spinal assembly there between.

In another embodiment, an apparatus is provided having a face portion with frictional character. The frictional character is to longitudinally stabilize the apparatus to a plate of a spinal assembly.

In another embodiment, a spinal assembly is provided with a vertebral screw, a spinal plate, an apparatus to secure the vertebral screw, and a connector brace to stabilize the plate. The plate has an uninterrupted passage to accommodate a portion of the vertebral screw there through.

In a method, a vertebral screw is placed through an opening of a connector brace and inserted into a vertebral body of a patient. The brace includes sidewalls to stabilize a spinal plate.

BRIEF DESCRIPTION OF THE DRAWINGS

FIG. 2 is a top view of the embodiment of spinal assembly plate shown in FIG. 1.

FIG. 3 is a perspective view of the embodiment of spinal assembly plate shown in FIG. 1 with an embodiment of a pedicle screw attached thereto.

DETAILED DESCRIPTION

While embodiments are described with reference to certain spinal assemblies, plates, connector braces, nuts, and other devices, embodiments are applicable to any implant to be secured to a vertebral body. This would include any methods, devices, or systems directed toward stabilization of the spine. The embodiments described here are particularly useful when two or more vertebrae of an individual are to be immobilized, such as by securing and fusing immediately adjacent vertebrae. Additionally, embodiments described can be useful in immobilizing vertebrae by being secured to vertebrae that are not necessarily immediately adjacent one another.

Figure 1:
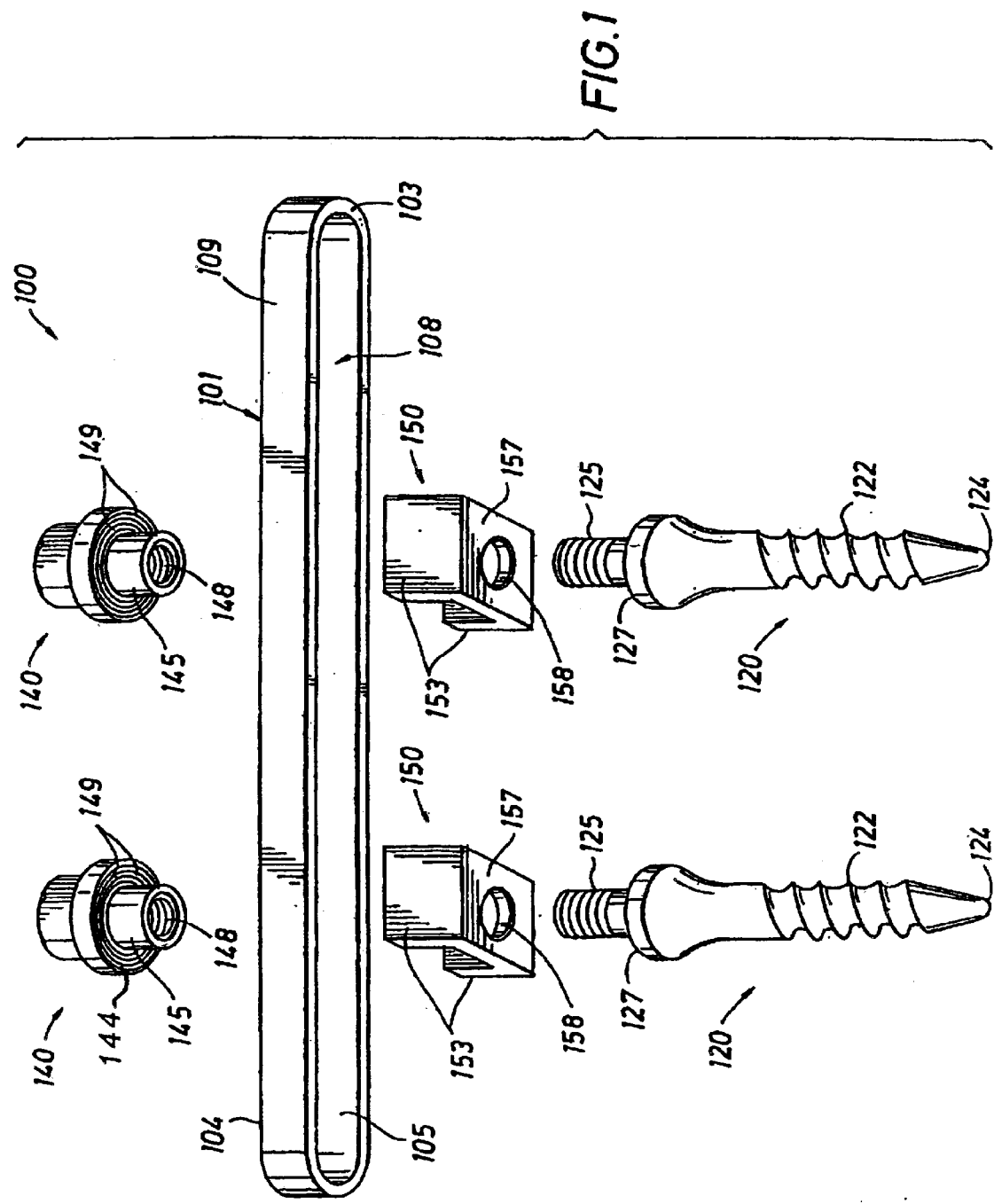
FIG. 1 is an exploded perspective view of an embodiment of a spinal assembly and plate.

Referring to FIG. 1, a spinal assembly 100 is shown. The spinal assembly 100 includes a plate 101 and at least one vertebral screw 120, nut 140, and connector brace 150. In one embodiment, all of the spinal assembly parts 101, 120, 140, 150 are made of pure titanium. In other embodiments other materials are used. However, when other materials are used, they are preferably a metal for combining with titanium to form spinal assembly parts 101, 120, 140, 150 of a titanium alloy.

Continuing with reference to FIG. 1, the plate 101 has an inner wall 105 and an outer wall 109. The inner wall 105 defines a passage 108 that is of an uninterrupted form. No bridge or other supportive structure intersects the passage 108, for example, to stabilize opposite sides of the inner wall 105 to one another. As discussed further herein, the resulting uninterrupted passage 108 allows unique positioning of vertebral screws 120 along the plate 101 in a non-predetermined manner.

As noted above, the passage 108 of the plate 101 is to accommodate a portion of at least one vertebral screw 120. In the embodiment shown, two vertebral screws 120 are shown. However, in other embodiments, additional vertebral screws 120 are to be accommodated by the plate 101. The vertebral screw 120 includes a first coupling mechanism, such as threading, referred to here as vertebral threading 122 to secure the vertebral screw 120 into a portion of a vertebrae. In one embodiment, the vertebral screw 120 is to be secured to a pedicle structure 522 of a vertebra (see FIG. 5). The vertebral screw 120 also includes a second coupling mechanism, such as threading, referred to here as nut threading 125 to be inserted through the passage 108 of the plate 101 and threadably into the nut 140 at the opposite side of the plate 101.

Embodiments of vertebral screws 120 can range from about 25 mm to about 75 mm in length as measured from a tip 124 of the vertebral screw 120 to a support 127 of the vertebral screw 120 where a connector brace 150 is to rest. Additionally, embodiments of vertebral screws 120 can range from about 4 mm to about 10 mm in diameter.

Continuing with reference to FIG. 1, an embodiment of a connector brace 150 is shown to be positioned between the support 127 of the vertebral screw 120 and a bottom surface 103 of the plate 101. The connector brace 150 includes a base 157 having an opening 158 to allow a portion of the vertebral screw 120 to pass through the connector brace 150 and the passage 108 of the plate 101. The support 127 of the vertebral screw 120 is larger than an outer diameter of the opening 158 of the connector brace 150. Thus, only the portion of the vertebral screw 120 above the support 127 can pass through the opening 158. The connector brace 150 also includes sidewalls 153. The sidewalls 153 rest adjacent opposite portions of the outer wall 109 when the spinal assembly 100 is assembled. As discussed further herein, the connector brace 150 and sidewalls 153 provide stability and prevent spreading of the plate 101 and widening of the passage 108 as the nut 140 is tightened in securing the vertebral screw 120 and plate 101.

Embodiments of connector braces 150 can be of many configurations and positioned in various manners. For example, in an alternate embodiment, the connector braces 150 include sidewalls 153 in the form of mating teeth rather than of a flat square shape (as shown). In another embodiment, a connector brace 150 can include multiple connector brace 150 portions having mating teeth shaped sidewalls 153 positioned at each vertebral screw 120 location along the plate 101. In such an embodiment, one connector brace portion rests atop the top surface 104 with mating teeth extending toward the vertebral screw 120 and the other connector brace portion rests below the bottom surface 103 of the plate 101 with mating teeth extending upward toward the top surface 104 of the plate 101. The mating teeth of the opposing connector brace portions interlock to stably secure the plate 101.

Continuing with reference to FIG. 1, an embodiment of a nut 140 is shown. The nut 140 includes a coupling portion 145 having a recess 148 to accommodate nut threading 125 of the vertebral screw 120. The nut 140 is of a diameter about the size of a width across the plate 101. As a result, a face 144 of the nut 140 can act against a top surface 104 of the plate 101 as the nut 140 is tightened about the nut threading 125 of the vertebral screw 120. As the nut 140 is tightened in this manner, the support 127 of the vertebral screw 120 is forced tightly against the base 157 of the connector brace 150. The face 144 of the nut 140 also becomes tighter against the top surface 104 of the plate 101.

As discussed further herein, the face 144 of the nut 140 is provided with a frictional character such as ridges 149 to prevent longitudinal slipping of the nut 140 across the top surface 104 of the plate 101 during tightening.

Referring to FIG. 2, a top view of the plate 101 of FIG. 1 is shown revealing all of its top surface 104. As shown, in FIGS. 1 and 2, the connector braces 150 are slidably below the plate 101 prior to securing of the spinal assembly 100 to a spine. The sidewalls 153 of the connector braces 150 rest adjacent opposite portions of the outer wall 109 of the plate 101. Embodiments of the plate 101 may have a width of between about 7 mm to about 13 mm from one side of the outer wall 109 to the other, preferably about 10 mm. Embodiments of the connector brace 150 can have a width from about 7.5 mm to about 13.5 mm from one side to the other of an inner surface 155 of the connector brace 150. In one embodiment, the width of the connector brace 150 as described, exceeds the width of the plate 101 by no more than about 0.3 mm to ensure a secure fit between the two.

Continuing with reference to FIGS. 1 and 2, the uninterrupted passage 108 allows unique positioning of vertebral screws 120 along the plate 101 in a non-predetermined manner. This is because as the connector brace 150 is slid into any position below the plate 101, the opening 158 is never obstructed by any portion of the plate 101. Rather, only the uninterrupted passage 108 is above the opening 158 at any position along the body of the plate 101. Thus, the nut threading 125 of a vertebral screw 120 can be inserted through the opening 158 at any longitudinal position along the plate 101. No predetermined positioning of the vertebral screw 120 with respect to the plate 101 is required. Therefore, the spinal assembly 100 can stabilize a variety of spine configurations where the distance between vertebrae or vertebrae portions to accommodate vertebral screws 120 can be widely variable.

Referring to FIG. 3, the spinal assembly 100 is shown with a vertebral screw 120 secured to the plate 101 by the nut 140. In the embodiment shown, the vertebral screw 120 does not directly contact the plate 101, but rather, the support 127 of the vertebral screw 120 is flush against the base 157 of the connector brace 150. The nut threading 125 of the vertebral screw 120 has been inserted through the opening 158 of the connector brace 150 and is received by the coupling portion 145 of the nut 140 (see FIG. 1). The coupling portion 145 of the nut 140 includes threading to receive and tighten about the nut threading 125 of the vertebral screw 120 (see FIG. 1).

As the nut 140 is tightened, compressive forces between the nut 140 and the support 127 of the vertebral screw 120 are transmitted to the plate 101 making the plate 101 susceptible to spreading. The plate 101 becomes more susceptible to spreading as lengths greater than about 40 mm are used (e.g. to accommodate more than two vertebral screws 120).

In order to prevent the plate 101 from spreading and the passage 108 widening, the connector brace 150 includes the aforementioned sidewalls 153. The sidewalls 153 brace the plate 101 and prevent widening of the passage 108 or any outward bulging of the plate 101 at the inner or outer walls 105, 109. Thus, the spinal assembly 100 remains secure and intact even as the nut 140 continues to tighten. In one embodiment the nut 140 is tightened to between about 8 Newton-meters (Nm) and about 15 Nm, preferably between 10 Nm and about 14 Nm, without causing the plate 101 to spread. In another embodiment the nut 140 can be tightened beyond about 15 Nm without causing the plate 101 to spread, even where the plate exceeds about 40 mm in length.

Embodiments of the nut 140 can range from about 5 mm to about 15 mm in diameter, preferably about 10 mm. Additionally, the nut 140 shown will be of a diameter large enough so that the nut 140 at least partially covers a portion of the top surface 104 of both sides of the plate 101. In one embodiment, the nut 140 is of a diameter as large as the width of the plate 101.

Figure 4:
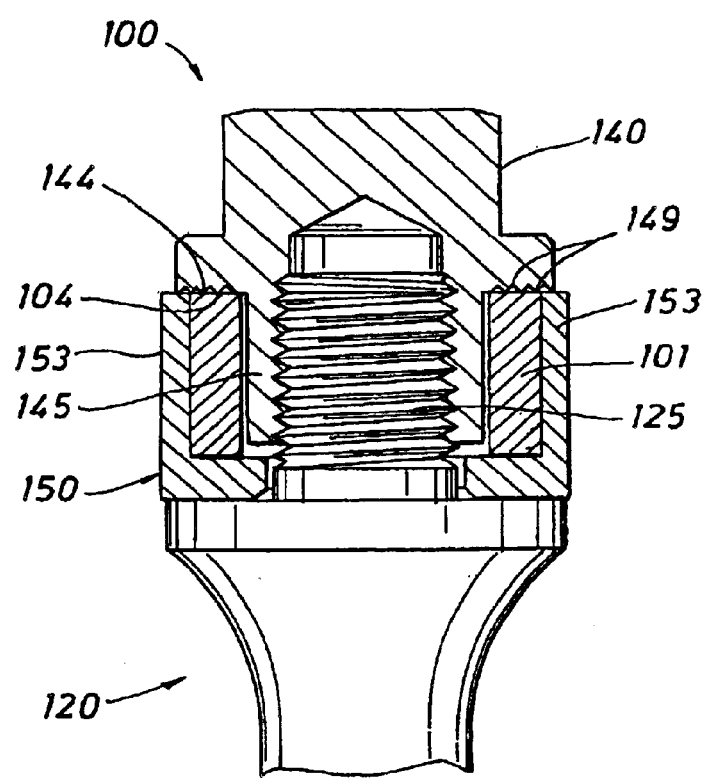
FIG. 4 is a cross-sectional view of the spinal assembly plate and pedicle screw of FIG. 3.

Referring to FIG. 4, a cross-sectional view of the spinal assembly 100 is shown. In the embodiment shown, the sidewalls 153 of the connector brace 150 can be seen secured about the plate 101. As the nut 140 is tightened, the plate 101 cannot spread open beyond the sidewalls 153.

Continuing with reference to FIG. 4, the nut threading 125 portion of the vertebral screw 120 is shown secured within the coupling portion 145 of the nut 140. As the nut 140 is tightened, the face 144 of the nut 140 compresses against the top surface 104 of the plate 101. To prevent longitudinal slipping of the nut 140 as it compresses against the top surface 104, frictional ridges 149 protrude from the face 144 of the nut 140 (see also FIG. 1). As the nut 140 compresses against the top surface 104, the shape of the face 144 of the nut 140 (e.g. including ridges 149) allows the nut 140 to grip the top surface 104 of the plate 101 preventing linear or longitudinal movement of the nut 140 across the top surface 104 of the plate 101.

Embodiments of the nut 140 include ridges 149 on the face 144 varying in number from about 3 to about 20, preferably between about 4 and about 6, depending on the diameter of the nut 140. Embodiments can include about 1 ridge for every 2 mm of nut 140 diameter. For example, in one embodiment the nut 140 is about 10.5 mm in diameter and includes about 5 ridges 149.

Figure 5:
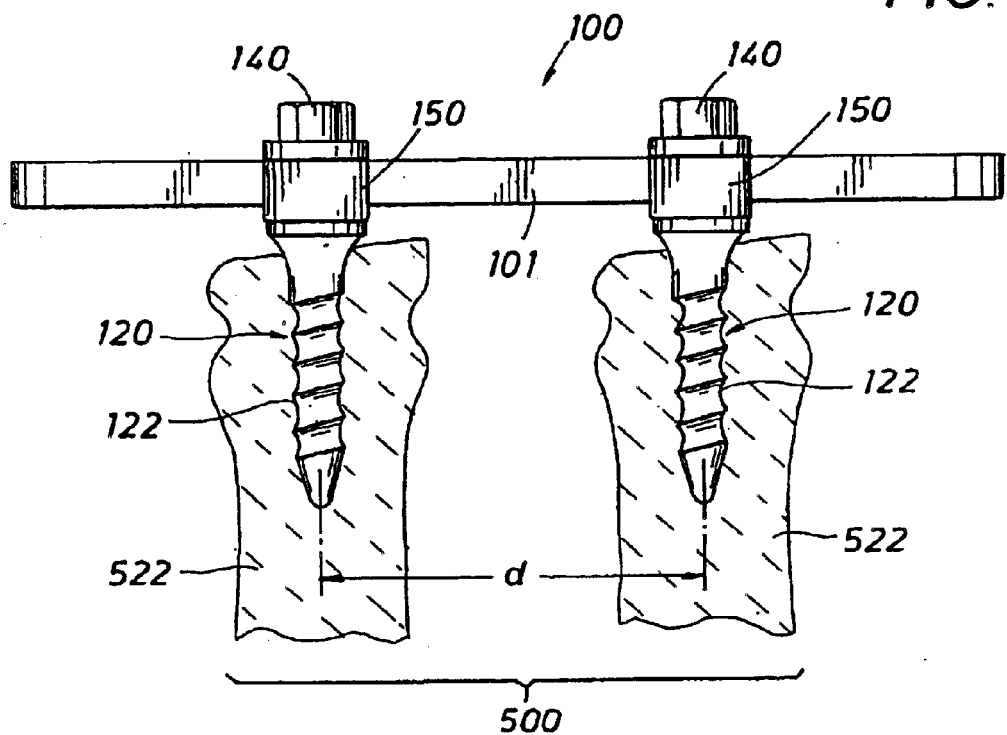
FIG. 5 is a side view of the embodiment of spinal assembly and plate shown in FIG. 1 secured to pedicle structures of a patient.

Referring to FIG. 5, the spinal assembly 100 is shown secured to a portion of a spine 500 of a patient. The vertebral screws 120 have been secured to pedicle portions 522 of the spine 500 via vertebral threading 122. Connector braces 150 and nuts 140 secure the plate 101 stably to the vertebral screws 120 as described above.

Continuing with reference to FIG. 5, the middle of each pedicle portion 522 is separated from the other by a given distance (d). In the embodiment shown, the vertebral screws 120 are to be secured into the middle of each pedicle portion 522. However, the given distance (d) can be highly variable from patient to patient, and even from one longitudinal position along the spine 500 to another within the same patient. Furthermore, the morphology of the spine 500 may require vertebral screws 120 be inserted into non-adjacent pedicle portions 522 in securing the spinal assembly 100. Thus, even greater variability in a distance between vertebral screws 120 can be required.

In spite of the above-described variability, the vertebral screw 120, as well as the connector brace 150 and nut 140, can be positioned at any longitudinal position along the plate 101. Therefore, precise and proper placement of the vertebral screws 120 is not sacrificed. In fact, the same spinal assembly 100 can be used in a variety of different patients or a variety of different spinal locations without regard to the particular longitudinal position to be occupied by vertebral screws 120 or the particular distance called for between adjacent vertebral screws 120. This flexibility is achieved in a manner that can include connector braces 150 which do not allow the plate 101 of the spinal assembly 100 to spread or deform. Additionally, the plate 101 can be securely gripped and stabilized in position by a nut 140 having frictional ridges 149 (see FIG. 4).

In a method, the spinal assembly 100 is installed by first placing the vertebral screws 120 into pedicle portions 522. The Connector braces 150 are then positioned over the placed vertebral screws 120. Openings 158 of the connector braces 150 accommodate nut treading 125 of the vertebral screws 120 (see FIG. 1). The spinal assembly plate 101 is then positioned within the connector braces 150 between sidewalls (see FIG. 1).

The spinal assembly plate 101 includes an uninterrupted passage 108 to accommodate the nut threading 125 of the vertebral screw 120. Nuts 140 are screwed about the nut threading 125 of each vertebral screw 120 to secure the spinal assembly plate 101 to the spine 500 (see FIG. 1).

Embodiments include an improved spinal assembly plate. Although exemplary embodiments describe particular spinal assembly parts including vertebral screws, connector braces, nuts, and a spinal plate, additional embodiments are possible. For example, in other embodiments multiple connector braces of differing configurations can be used at each vertebral screw location along the plate. Additionally, many changes, modifications, and substitutions may be made without departing from the spirit and scope of these embodiments.

I claim:

1. A spinal assembly plate comprising:
an elongated body having a longitudinal dimension suitable to be secured to a portion of a spine and having an uninterrupted, longitudinally extending passage defining an inner wall, said passage having a dimension to extend over a portion of said spine and to accommadate a portion of at least one vertebral screw extending therethrough at a non-predetermined position within the passage selected from boundless potential longitudinal positions, and said elongated body including an uninterrupted, longitudinally extending perimeter defining an outer wall a connector brace having a sidewall extending a portion of a length of said outer wall in a direction defined by an axis of the vertebral screw to couple adjacent said outer wall at a non-predetermined position along the perimeter selected from boundless potential longitudinal positions, and a nut having a face configured to be secured adjacent a surface of said elongated body and a coupling portion to secure said portion of said vertebral screw.

2. The spinal assembly plate of claim 1, wherein said elongated body further comprises a surface configured to be oriented towards said portion of said spine between an outer wall and said inner wall.

3. The spinal assembly plate of claim 2 wherein said base of the connector brace comprises a dimension to accommodate said portion of said at least one vertebral screw between said base and said sidewall.

4. A kit comprising:
a plate having a longitudinal dimension suitable to be secured to a portion of a spine, having an uninterrupted, longitudinally extending passage having a dimension to extend over a portion of the spine, and having an uninterrupted, longitudinally extending perimeter defining an outer wall;
a nut having dimension to couple to the plate and to extend through the plate at a non-predetermined longitudinal position within the passage selected from an undetermined longitudinal adjustment distance within the passage; and
a connector brace having a dimension to couple adjacent said outer wall at a non-predetermined position along the perimeter selected from boundless potential longitudinal positions.

5. The kit of claim 4, further comprising a vertebral screw to couple to the nut.

6. The kit of claim 5, wherein a portion of the vertebral screw and the a portion of the nut are cooperatively threaded.

7. The kit of claim 5, further comprising said connector brace is to stabilize the plate as the nut secures the vertebral screw.

8. The kit of claim 5, wherein the nut has a face portion having a frictional character to longitudinally stabilize the nut to the plate when the vertebral screw is coupled to the nut and the vertebral screw is secured to a vertebral body of a patient.

9. The kit of claim 8, wherein the frictional character is provided by at least one frictional ridge protruding from the face portion.

10. The of claim 9, wherein the face portion has an approximately circular circumference and the at least one frictional ridge includes a plurality of frictional ridges defining concentric circles of the face portion.

11. A spinal assembly plate comprising:

an elongated body having a longitudinal dimension suitable to be secured to a portion of a spine and having an uninterrupted, longitudinally extending passage defining an inner wall, said passage having a dimension to extend over a portion of said spine and to couple to a portion of at least one vertebral screw extending therethrough at a non-predetermined position within the passage selected from boundless potential longitudinal positions, and said elongated body including an uninterrupted, longitudinally extending perimeter defining an outer wall having a dimension such that a sidewall of a connector brace may be coupled adjacent said outer wall at a non-predetermined position along the perimeter selected from boundless potential longitudinal positions;

wherein said elongated body further comprises a surface configured to be oriented towards said portion of said spine between said outer wall and said inner wall and said plate further comprises a connector brace, having a sidewall to be adjacent said outer wall and a base to be adjacent said surface oriented towards said portion of said spine:

wherein the surface of said elongated body is a first surface, the elongated body further comprising a second surface terminating at said inner wall, said plate further comprising:

a nut having a face configured to be secured adjacent said second surface of said elongated body and a coupling portion to secure said portion of said vertebral screw.

12. The spinal assembly plate of claim 11 wherein said nut is to effect a torque of between about 8 Nm and about 15 Nm when said plate and said portion of said vertebral screw are secured by said nut.

13. The spinal assembly plate of claim 12 wherein said elongated body has a uniform shape and a length greater than about 40 mm, said elongated body to maintain said uniform shape as said plate and said portion of said vertebral screw are secured.

* * * * *